United States Patent [19]

Fukuto et al.

[11] 3,997,549

[45] Dec. 14, 1976

[54] N-ARYLSULFENYLATED DERIVATIVES OF BENZOFURANYL METHYLCARBAMATES

[75] Inventors: Tetsuo Roy Fukuto; Allan L. Black, both of Riverside, Calif.

[73] Assignee: The Regents of the University of California, Berkeley, Calif.

[22] Filed: Mar. 12, 1973

[21] Appl. No.: 340,507

[52] U.S. Cl. .................. 260/306.6 A; 260/340.5; 260/346.2 R; 424/247; 424/285

[51] Int. Cl.² ............ C07D 277/38; C07D 317/10; C07D 307/76

[58] Field of Search ............... 260/306.6 A, 340.5, 260/346.2 R

[56] References Cited

UNITED STATES PATENTS 3,847,951  11/1974  Kohn et al. .................. 260/346.2

FOREIGN PATENTS OR APPLICATIONS 7,100,959  8/1972  South Africa

OTHER PUBLICATIONS

Serban et al. Chem. Abstracts vol. 78, Abstract No. 124326r (1973).

*Primary Examiner*—Anton H. Sutto
*Attorney, Agent, or Firm*—Robert L. Andersen; Henry R. Ertelt

[57] ABSTRACT

A new class of chemical compounds useful for the control of insects consists of (methyl) (arylsulfenyl)-carbamic acid esters of 2,3-dihydro-2,2-dimethyl-7-benzofuranol. The preparation of these compounds, their physical properties, formulation, and use to control both household insects and crop insects are exemplified.

3 Claims, No Drawings

N-ARYLSULFENYLATED DERIVATIVES OF BENZOFURANYL METHYLCARBAMATES

This invention pertains to the general field of pesticides and in particular to the area of insecticides for the control of both household insects and crop insects.

The compounds of this invention are N-arylsulfenyl derivatives of 2,3-dihydro-2,2-dimethyl-7-benzofuranyl methylcarbamate, known by the common name carbofuran. Carbofuran, a potent insecticide, is described in U.S. Pat. No. 3,474,171, issued Oct. 21, 1969.

The N-arylsulfenyl derivatives of carbofuran are more effective against certain pests and lower in mammalian toxicity than is carbofuran. These highly effective derivatives of carbofuran have not previously been described.

The new class of insecticidal compounds of this invention has the formula

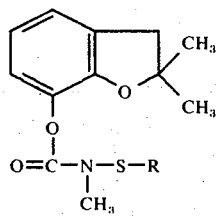

where R is a mono- or bi-cyclic aromatic group. Examples of suitable R groups include unsubstituted phenyl, phenyl substituted with one or more halogen, lower alkyl, lower alkoxy, methylenedioxy, or cyano; naphthyl, or benzothiazolyl. For the purposes of this application the term "lower" means having 1 to 4 carbon atoms.

Preferred insecticidal carbofuran derivatives of this invention are those compounds in which the R group is phenyl substituted with from 1 to 3 groups selected from the group consisting of chlorine, bromine, lower alkyl, and lower alkoxy.

The preparation and insecticidal properties of the compounds of this invention are illustrated in the following specific examples, which are provided only by way of illustration and not of limitation. All temperatures are in degrees centigrade, Unless otherwise specified, concentration of liquid volumes was carried out under the reduced pressure produced by a water aspirator.

EXAMPLE I

Synthesis of 2,3-Dihydro-2,2-dimethyl-7-benzofuranyl (methyl) (phenylthio)carbamate A. Preparation of benzenesulfenyl chloride Sulfuryl chloride (135g) was added slowly during one hour to a solution of 110 g of thiophenol in 500 ml of carbon tetrachloride at room temperature. Three 2-ml quantities of pyridine were added at intervals during the addition. The solution was heated on the steam bath (about 60°) for two hours. Half the mixture was concentrated under reduced pressure and the red liquid residue was distilled under nitrogen to give 69 g of benzenesulfenyl chloride, b.p. 49° at 2.0 mm, $n_D^{25}$ 1.6070.

B. Benzenesulfenation of carbofuran

A solution of 11 g of carbofuran in 50 ml of pyridine was added to 14.5 g of benzenesulfenyl chloride and the mixture was allowed to stand overnight at room temperature. The mixture was filtered, 250 ml of dry ether was added to the filtrate and the mixture refiltered. The filtrate was concentrated under reduced pressure. The residue was washed by stirring with 50 ml of water for one hour at room temperature. When the oily product was stirred with 200 ml of hexane, about 80% dissolved. The hexane solution was decanted, washed six times with water, then with saturated aqueous sodium chloride solution, then dried over sodium sulfate. The dried solution was concentrated under reduced pressure and the residue distilled to give a colorless liquid, b.p. 168°–174° at 0.005 mm. Redistillation gave 2,3-dihydro-2,2-dimethyl-7-benzofuranyl (methyl) (phenylthio)carbamate, b.p. 168° at 0.005 mm, $n_D^{25}$ 1.5758. This compound crystallized upon standing, m.p. 66°. The n.m.r. spectrum was consistent with the assigned structure.

Analysis: Calc'd for $C_{18}H_{19}NO_2S$: C 67.80; H 6.32; Found: C 67.39; H 6.02.

EXAMPLE II

Synthesis of 2,3-Dihydro-2,2-dimethyl-7-benzofuranyl (methyl)(2-methylphenylthio)carbamate A. Preparation of 2-methylbenzenesulfenyl chloride A solution of 27.2 g of sulfuryl chloride in 50 ml of dry carbon tetrachloride was added dropwise to a cold (ice-salt bath) solution of 25 g of 4-methylbenzenethiol in 50 ml of carbon tetrachloride containing a few drops of pyridine. The solution was stirred for 0.5 hour at ice-salt bath temperature, allowed to warm to room temperature, then heated under gentle reflux for 0.5 hour. The solution was filtered through a layer of anhydrous sodium sulfate and the filtrate concentrated under reduced pressure. The red liquid residue was distilled to give 24.1 g of 2-methylbenzenesulfenyl chloride, b.p. 67°–69° at 2 mm, $n_D^{25}$ 1.6015.

B. 2-Methylbenzenesulfenation of carbofuran

A solution of 12 g of freshly prepared 2-methylbenzenesulfenyl chloride in 50 ml of dry pyridine was added to a solution of 16.6 g of carbofuran in 50 ml of pyridine. An exothermic reaction occurred. The mixture was allowed to stand overnight, filtered and poured into 250 ml of water. The oil which separated was washed with water and the washed oil extracted with 300 ml of hexane. The hexane solution was filtered, then washed five times with 100-ml portions of water and dried. Concentration under reduced pressure gave a solid which on recrystallization from hexane gave 13.6 g of white solid, m.p. 75°–6°. Three recrystallizations from hexane gave white solid 2,3-dihydro-2,-2-dimethy-7-benzofuranyl (methyl)(2-methylphenylthio)-carbamate, m.p. 78°. The n.m.r. spectrum was consistent with the assigned structure.

Analysis: Calc'd for $C_{19}H_{21}NO_3S$: C 66.47; H 6.12; Found: 66.29; H 6.21.

EXAMPLE III

Synthesis of 2,3-Dihydro-2,2-dimethyl-7-benzofuranyl (4-tert-butylphenylthio)(methyl)carbamate Sulfuryl chloride (13.5 g) was added dropwise to a solution of 16.9 g of 4-(tert-butyl)benzenethiol in 75 ml of pyridine while the mixture was cooled in an ice bath. Stirring and cooling was continued for 0.5 hour after addition was completed, then the cooling bath removed and stirring continued another 0.5 hour.

One-half (by volume) of the resultant solution of 4-(tert-butyl)benzenesulfenyl chloride was added to a solution of 10.9 g of carbofuran in 30 ml of pyridine. The mixture was allowed to stand overnight, then poured into water. The water-insoluble material was washed several times with water, then dissolved in ether. The ether solution was washed with water and dried. Removal of the ether under reduced pressure gave a solid which on recrystallization from hexane-ether gave 7.5 g of solid, m.p. 120°–3°. Four recrystallizations from hexane gave 2,3-dihydro-2,2-dimethyl-7-benzofuranyl [4-(tert-butyl)phenylthio](methyl)carbamate, m.p. 122°–123°. The n.m.r. spectrum was consistent with the assigned structure.

Analysis: Calc'd for $C_{22}H_{27}NO_3S$: C 68.57; H 7.01; Found: C 68.38; H 7.12.

EXAMPLE IV

Synthesis of 2,3-Dihydro-2,2-dimethyl-7-benzofuranyl(methyl)(4-methylphenylthio)carbamate A solution of 8.75 g of 4-methylbenzenesulfenyl chloride in 25 ml of pyridine was added to a solution of 10.9 g of carbofuran in 25 ml of pyridine. A precipitate formed immediately. The reaction mixture was processed as described in Example I to give a residue which could not be distilled even at 0.005 mm. Passage through a falling film still at 140° at 0.01 mm, then at 168° at 0.01 mm gave a liquid which crystallized on standing to a solid, m.p. 62°. Recrystallization several times from petroleum ether gave 2,3-dihydro-2,2-dimethyl-7-benzofuranyl (methyl)(4-methylphenylthio)carbamate, m.p. 65°.

Analysis: Calc'd for $C_{19}H_{21}NO_3S$: C 66.47; H 6.12; Found: C 66.71; H 5.72.

RESYNTHESIS

In a resynthesis, 45.1 g of sulfuryl chloride was added during one hour to a cold (ice bath) solution of 41.4 g of 4-methylbenzenethiol in 150 ml of pyridine. The mixture was allowed to warm to room temperature (0.5 hour) and to it was added a solution of 60 g of carbofuran in 50 ml of pyridine. This mixture was allowed to stand overnight, filtered and the filtrate poured into one liter of water. The water was decanted and the oil dissolved in hexane. The insoluble, unreacted carbofuran was removed by filtration and the solution seeded. The solid which separated was recrystallized to give 12.5 g of 2,3-dihydro-2,2-dimethyl-7-benzofuranyl (methyl) (4-methylphenylthio)carbamate, m.p. 64°.

EXAMPLE V

Synthesis of 2,3-Dihydro-2,2-dimethyl-7-benzofuranyl (4-chlorophenylthio) (methyl)carbamate A solution of 12.7 g of 4-chlorobenzenesulfenyl chloride in 25 ml of pyridine was added to a solution of 13 g of carbofuran in 25 ml of pyridine. The mixture was allowed to stand for four hours then treated as described in Example II. The heavy oil was passed through a falling film still at successively higher temperatures of 120° and 140° at 0.005 mm, gave at 164° at 0.005 mm a product having an n.m.r. spectrum consistent with the assigned structure. Recycling at 168° at 0.005 mm gave 7.1 g of 2,3-dihydro-2,2-dimethyl-7-benzofuranyl (4-chlorophenylthio) (methyl)carbamate, which crystallized on standing to a solid, m.p. 73° (from petroleum ether/ether).

Analysis: Calc'd for $C_{18}H_{18}ClNO_3S$: C 59.44; H 4.95; Found: C 59.38; H 4.92.

EXAMPLE VI

Synthesis of 2,3-Dihydro-2,2-dimethyl-7-benzofuranyl [4-(tert-butyl)-2-methylphenylthio] (methyl)carbamate 4-(tert-Butyl)-2-methylbenzenesulfenyl chloride (13.3 g) was added to a solution of 13.6 g of carbofuran in 40 ml of pyridine and the mixture set overnight. The mixture was treated as described in Example II to give 17.2 g of 2,3-dihydro-2,2-dimethyl-7-benzofuranyl [4-(tert-butyl)-2-methylphenylthio] (methyl)carbamate, m.p. 104°–5°. Recrystallization from hexane increased the melting point to 109°.

Analysis: Calc'd for $C_{23}H_{29}NO_3S$: C 69.17; H 7.27; Found: C 69.60; H 6.57.

EXAMPLE VII

Synthesis of 2,3-Dihydro-2,2-dimethyl-7-benzofuranyl (2-benzothiazolylthio) (methyl)carbamate A solution of 6.75 of sulfuryl chloride in 20 ml of benzene was added dropwise, with vigorous stirring under nitrogen, to a solution of 8.4 g of 2-mercaptobenzothiazole in 150 ml of benzene. The mixture was heated slowly to reflux and maintained under gentle reflux until evolution of hydrogen chloride had ceased. A solution of 11 g of carbofuran in 150 ml of pyridine was added dropwise and the mixture stirred for two hours at reflux under nitrogen. The mixture was poured into water. The organic phase was separated, washed with dilute hydrochloric acid, water and saturated aqueous sodium chloride, then dried. The dry solution was concentrated under reduced pressure and the residue recrystallized from ethanol to give 2,3-dihydro-2,2-dimethyl-7-benzofuranyl (2-benzothiazolylthio) (methyl)carbamate, m.p. 92°–3°. Recrystallization from hexane-benzene increased the melting point to 97°. The n.m.r. spectrum was consistent with the assigned structure.

Analysis: Calc'd for $C_{19}H_{18}N_2O_3S_2$: C 59.07; H 4.66; Found: C 58.82; H 4.76.

Prepared in a similar manner were:

EXAMPLE VIII 2,3-Dihydro-2,2-dimethyl-7-benzofuranyl (4-bromophenylthio) (methyl)carbamate This compound was prepared by the method of Example II; m.p. 60°.

EXAMPLE IX 2,3-Dihydro-2,2-dimethyl-7-benzofuranyl (4-methoxyphenylthio) (methyl)carbamate This compound was prepared by the method of Example III; m.p. 80°.

EXAMPLE X 2,3-Dihydro-2,2-dimethyl-7-benzofuranyl (3-methylphenylthio) (methyl)carbamate This compound was prepared by the method of Example VI; b.p. 185° at 0.005 mm, $n_D^{25}$ 1.5758.

EXAMPLE XI 2,3-Dihydro-2,2-dimethyl-7-benzofuranyl (4-bromo-2-methylphenylthio) (methyl)carbamate This compound was prepared by the method of Example VI; m.p. 81°.

EXAMPLE XII 2,3-Dihydro-2,2-dimethyl-7-benzofuranyl (2-isopropylphenylthio) (methyl)carbamate This compound was prepared by the method of Example VI; b.p. 182° at 0.005 mm; m.p. 71°.

EXAMPLE XIII 2,3-Dihydro-2,2-dimethyl-7-benzofuranyl (2,4-dimethylphenylthio) (methyl)carbamate This compound was prepared by the method of Example VI; b.p. 179° at 0.005 mm; m.p. 39°.

EXAMPLE XIV 2,3-Dihydro-2,2-dimethyl-7-benzofuranyl (methyl)-(3,4-methylenedioxyphenylthio)carbamate This compound was prepared by the method of Example VI; m.p. 80°.

EXAMPLE XV 2,3-Dihydro-2,2-dimethyl-7-benzofuranyl (4-cyanophenylthio) (methyl)carbamate This compound was prepared by the method of Example VI; m.p. 126°.

EXAMPLE XVI 2,3-Dihydro-2,2-dimethyl-7-benzofuranyl (methyl)-(pentachlorophenylthio)carbamate This compound was prepared by the method of Example VII; m.p. 153°–4°. While the melting point is identical to that of carbofuran, the n.m.r. spectrum and elemental analyses were both consistent with the assigned structure.

EXAMPLE XVII 2,3-Dihydro-2,2-dimethyl-7-benzofuranyl (methyl)-(2-naphthylthio)carbamate This compound was prepared by the method of Example VII; m.p. 77°–8°.

EXAMPLE XVIII

Toxicity to Houseflies

Toxicity of the compounds of the present invention to houseflies was tested using the technique described by March and Metcalf in Bull. Calif. State Dept. Agr. 38, No. 2, 93–101(1949): Solutions of test compounds in acetone were prepared at a range of concentrations. Adult female houseflies were treated with one drop of acetone solution, applied to the prothorax, using a syringe calibrated to deliver 1.00 ± 0.05 mm³ drops. Twenty flies were treated at each dosage, each test compound was applied at 8 to 10 dosage levels. Each test was replicated three times. Following treatment each lot of flies was confined in paper-lined one-quart cylindrical cartons, the solid ends of which had been replaced with wire screen. A one-inch square of cotton saturated with 40% sugar solution was provided for food in each carton. The cartons of flies were held in a constant temperature chamber at 60° F and 60% relative humidity for 24 hours before mortality counts were made. Flies totally unable to make crawling or walking movements were counted as dead. $LD_{50}$ values were calculated in the conventional manner. The results are presented in Table 1. The test compounds ranged in toxicity from twice as toxic to one-tenth as toxic as the parent carbofuran.

EXAMPLE XIX

Toxicity to Mosquitoes

Toxicity of the compounds of the present invention to mosquitoes was tested using the technique described in a Mulla, Metcalf and Geib in Mosquito News 28, No. 2, 236(1966): A one percent (w/v) stock solution was prepared by dissolving the test compound in acetone. The appropriate amount of stock solution was added with stirring to 100 ml of tap water and 20–25 fourth instar larvae of *Culex fatigans* were placed in the solution. After twenty-four hours, the counts were taken. Larvae not able to rise to the surface on touch were counted as dead. Each concentration was run in duplicate and each material was run on two or three different days. The average percent mortality was plotted against the logarithm of the concentration (in ppm) and the $LC_{50}$ value determined by inspection. The results are presented in Table 1. All compounds tested were more toxic to mosquitoes than the parent carbofuran. Improvements ranged from twofold to 25-fold.

EXAMPLE XX

Toxicity to Mice

Acute oral toxicity of the compounds of the present invention to mice was determined after the manner of Hollingworth, Fukuto, and Metcalf in J. Agr. Food Chem. 15, 235(1967): Solutions of the compounds at each of a series of concentrations were prepared in olive oil or propylene glycol as solubility required. A dose of 0.25 ml of each solution was administered to each of four female white Swiss mice using the "bolus" - tipped syringe. The mice were closely observed during the one to two hours immediately after treatment during which most of the mortality occurred. Final mortality determinations were made forty-eight hours after treatment. Results are presented in Table 1. $LD_{50}$ values were numerically from five to 75 times greater than that obtained for the parent carbofuran, indicating that the compounds of the present invention are all less toxic than the parent.

Table 1

| Compound of Example | Toxicity to Houseflies, Mosquitoes, Mice | | |
|---|---|---|---|
| | Houseflies $LD_{50}$(mg/kg) | Mosquitoes $LC_{50}$(ppm) | Mice $LD_{50}$(mg/kg) |
| I | 9.3 | 0.0045 | 25–50 |
| II | 3.7 | 0.004 | 100–125 |
| III | 2.7 | 0.0025 | 75 |
| IV | 9.0 | 0.0045 | 100–125 |
| V | 12.5 | 0.002 | 50 |
| VI | 7.5 | 0.002 | 75–125 |
| VII | 8.5 | 0.0095 | 50 |
| VIII | 9.0 | 0.004 | 50–75 |
| IX | 7.8 | 0.006 | 25–50 |
| X | 6.5 | 0.004 | 25–50 |
| XI | 11.25 | 0.0025 | 100–150 |
| XII | 8.3 | 0.003 | 50–75 |
| XIII | 9.0 | 0.003 | 50–100 |
| XIV | 5.0 | 0.0065 | 10–25 |
| XV | 22.5 | 0.022 | 25–50 |
| XVI | 26.5 | 0.0085 | 50 |

Table 1-continued

| Compound of Example | Toxicity to Houseflies, Mosquitoes, Mice | | |
|---|---|---|---|
| | Houseflies $LD_{50}$(mg/kg) | Mosquitoes $LC_{50}$(ppm) | Mice $LD_{50}$(mg/kg) |
| XVII | 8.0 | 0.0032 | 40 |
| Carbofuran | 6.7 | 0.052 | 2 |

EXAMPLE XXI

Toxicity to Crop Insects

Initial Contact Activity: One-half gram of test compound was dissolved in 40 ml of acetone and this solution was dispersed in 360 ml of water containing one drop of isooctyl phenyl polyethoxyethanol. An aliquot of this solution was diluted with water to provide a solution containing 1250 ppm of active ingredient. Test organisms and techniques were as follows: The activities against the Mexican bean beetle (*Epilachna varivestis* Muls.) and the southern army worm (*Prodenia eridania* [Cram.]) were evaluated by dipping the leaves of pinto bean plants into the test solution and infesting the leaves with the appropriate immature form insects when the foilage had dried; the activity against the pea aphid (*Macrosiphum pisi* [Harris]) was evaluated on broad bean plants whose leaves were dipped before infestation with adult aphids; the activity against the two-spotted spider mite (*Tetranychus urticae* [L.]) was evaluated on pinto bean plants whose leaves were dipped after infestation with adult mites; the activities against the milkweed bug (*Oncopeltus fascinatus* [Dallas]) and the plum curculio (*Conotrachelus nenuphar* [Herbst]) were evaluated by spraying the test solutions into glass dishes containing the adult insects; the activities against the granary weevil (*Sitophilus granarius* [L.]) and the confused flour beetle (*Tribolium confusum* [duVal]) were evaluated by introducing the insects into glass dishes which had been previously sprayed with test solution and allowed to dry. All organisms in the test were maintained in a holding room at 80° F. and 50% relative humidity for an exposure period of forty-eight hours. At this time the number of dead and living insects were counted and the percent kill was calculated. Results of these tests are summarized in Table 2, which shows the compounds to be effective against a broad range of insects.

Residual Contact Activity:

The residual contact activity of the compounds was determined on the same organisms using the technique described above, except that in each case the treated surface was allowed to dry and was exposed to normal light and air for seven days before introduction of the mites or insects. Results of these tests are summarized in Table 3. The compounds show a high order of residual activity toward the test insects.

Table 2

| Compound of Example | Initial Contact Toxicity to Crop Insects (% Kill at 1250 ppm) | | | | | | | |
|---|---|---|---|---|---|---|---|---|
| | BB | AW | PA | SM | MWB | PC | GW | FB |
| II | 100 | 100 | — | 28 | 100 | 100 | 100 | 98 |
| III | 100 | 100 | — | 27 | 100 | 100 | 100 | 100 |
| IV | 100 | 100 | — | 100 | 100 | 100 | 100 | 100 |
| V | 100 | 100 | 100 | 100 | 100 | 100 | 100 | — |
| VI | 100 | 95 | 0 | 77 | 100 | 100 | 100 | 90 |
| VII | 91 | 62 | 100 | 72 | 100 | 100 | 100 | — |
| X | 100 | 100 | 100 | 100 | 100 | 100 | 100 | 100 |
| XI | 100 | 100 | 35 | 9 | 100 | 100 | 100 | — |
| XIV | 100 | 100 | 100 | 38 | 100 | 100 | 100 | — |
| XVI | 100 | 0 | 100 | 4 | 95 | 90 | 100 | — |

BB:Mexican bean beetle
AW:southern army worm
PA:pea aphid
SM:two-spotted spider mite
MWB:milkweed bug
PC:plum curculio
GW:granary weevil
FB:confused flour beetle Table 3

| Compound of Example | Residual Contact Toxicity to Crop Insects (% Kill at 1250 ppm; 7 days) | | | | | | | |
|---|---|---|---|---|---|---|---|---|
| | BB | AW | PA | SM | MWB | PC | GW | FB |
| II | 100 | 100 | — | 13 | 100 | 100 | 100 | 98 |
| III | 100 | 31 | — | 2 | 100 | 95 | 100 | 100 |
| IV | 100 | 100 | — | 94 | 100 | 100 | 100 | 92 |
| V | 100 | 100 | 95 | 5 | 100 | 95 | 100 | — |
| VI | 100 | 100 | 0 | 7 | 95 | 53 | 100 | 100 |
| VII | 100 | 100 | 0 | 5 | 100 | 55 | 100 | — |
| X | 100 | 100 | 100 | 30 | 100 | 95 | 100 | 100 |
| XI | 100 | 100 | 10 | 3 | 95 | 40 | 100 | — |
| XIV | 100 | 100 | 10 | 2 | 100 | 80 | 100 | — |
| XVI | 100 | 40 | 10 | 8 | 30 | 10 | 92 | — |

BB:Mexican bean beetle
AW:southern army worm
PA:pea aphid
SM:two-spotted spider mite
MWB:milkweed bug
PC:plum curculio
GW:granary weevil
FB:confused flour beetle

EXAMPLE XXII

Systemic Insecticidal Activity

Favorable results in hydroponic testing using Mexican bean beetle and two-spotted spider mites were indicative of systemic activity, which was confirmed by further tests utilizing the soil-watering technique. Test organisms were Mexican bean beetle, southern army worm, pea aphid, and two-spotted spider mite on plants as described in Example XXI. Using appropriate precautions to avoid contamination of the test plant surfaces, a test solution prepared as in Example XXI so as to contain 156 ppm, was poured evenly over the surface of the soil in which the plant was growing. The treated plants were maintained under normal growing conditions for three days to permit translocation of the toxicant, after which the leaves were infested. Two days after infestation counts of living and dead insects were made. These results are summarized in Table 4, and results of similar tests utilizing test solutions of 39 ppm are summarized in Table 5. A high order of systemic activity is characteristic of compounds of the present invention.

Table 4

| Compound of Example | Systemic Toxicity to Crop Insects (% Kill at 156 ppm) | | | |
|---|---|---|---|---|
| | BB | AW | PA | SM |
| II | 100 | 100 | — | /5 |
| III | 100 | 0 | 43 | /4 |
| IV | 100 | 100 | — | /64 |
| V | 100 | 80 | 100 | 33/ |
| VI | 100 | 0 | 95 | /6 |
| VII | 81 | 60 | 100 | 2/ |
| X | 100 | 100 | 100 | /28 |
| XI | 100 | 100 | 100 | 28/ |
| XIV | 94 | 64 | 100 | 16/ |
| XVI | 60 | 0 | 45 | 1/ |
| Carbofuran | 100 | 100 | 100 | 43/70* |

BB:Mexican bean beetle
AW:southern army worm
PA:pea aphid
SM:two-spotted spider mite
*Two groups of compounds were compared with carbofuran in separate tests.

Table 5

| Compound of Example | Systemic Toxicity to Crop Insects (% Kill at 39 ppm) | | | |
|---|---|---|---|---|
| | BB | AW | PA | SM |
| II | 100 | /85 | 100 | /5 |
| III | 56 | /0 | 5 | /1 |
| IV | 100 | /100 | 100 | /24 |
| V | 95 | 50/ | 100 | 29/ |
| VI | 85 | /0 | 35 | /11 |
| VII | 68 | 0/ | 100 | 3/ |
| X | 100 | /100 | 100 | /26 |
| XI | 95 | 75/ | 100 | 23/ |
| XIV | 90 | 14/ | 100 | 10/ |
| XVI | 74 | 0/ | 0 | 1/ |
| Carbofuran | 100 | 50/100* | 100 | 5/3* |

BB:Mexican bean beetle
AW:southern army worm
PA:pea aphid
SM:two-spotted spider mite
*Two groups of compounds were compared with carbofuran in separate tests.

The insecticidal (methyl) (arylsulfenyl)-carbamic acid esters of 2,3-dihydro-2,2-dimethyl-7-benzofuranol may be formulated with the usual additives and extenders used in the preparation of insecticidal compositions. The toxicants of this invention, like most insecticidal agents, are generally not applied full strength, but are incorporated with the adjuvants and carriers normally employed for facilitating the dispersion of active ingredients, recognizing the accepted fact that the formulation and mode of application of a toxicant may affect the activity of the material. The present compounds may be applied, for example, as a spray, dust, or granule, to the area in which pest control is desired, the choice of application varying of course with the type of insect and the environment. Thus, these (methyl)-(arylsulfenyl)carbamic esters of 2,3-dihydro-2,2-dimethyl-7-benzofuranol may be formulated as granules of large particle size, as powdery dusts, as wettable powders as emulsifiable concentrates, as solutions, and the like.

Dusts are admixtures of the active ingredients with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as dispersants and carriers for the toxicant. These finely divided solids have an average particle size of less than about 50 microns. A typical dust formulation useful herein contains 10.0 parts of 2,3-dihydro-2,2-dimethyl-7-benzofuranyl (methyl) (4-methylphenylthio)carbamate, 30.0 parts of bentonite clay, and 60.0 parts of talc.

The compounds of the present invention may be made into liquid concentrates by solution or emulsion in suitable liquids, and into solid concentrates by admixtures with talc, clays and other known solid carriers used in the insecticide art. The concentrates are compositions containing about 5–50% toxicant, and 95–50% inert material which includes dispersing agents, emulsifying agents, and wetting agents. The concentrates are diluted for practical application, with water or other liquid for sprays or with additional solid carrier for use as dusts. Typical carriers for solid concentrates (also called wettable powders) include fuller's earth, kaolin clays, silicas, and other highly absorbent, readily wet inorganic diluents. A solid concentrate formulation useful herein contains 1.5 parts each of sodium lignosulfonate and sodium laurylsulfate as wetting agents, 25.0 parts of 2,3-dihydro-2,2-dimethyl-7-benzofuranyl (methyl) (2-methylphenylthio) carbamate and 72.0 parts of bentonite clay.

Useful liquid concentrates include the emulsifiable concentrates, which are homogeneous liquid or paste compositions readily dispersed in water or other dispersant, and may consist entirely of the toxicant with a liquid or solid emulsifying agent, or may also contain a liquid carrier such as xylene, heavy aromatic naphthas, isophorone and other nonvolatile organic solvents. For application, these concentrates are dispersed in water or other liquid carrier, and normally applied as a spray to the area to be treated.

Typical wetting, dispersing or emulsifying agents used in insecticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commence. The surface-active agent, when used, normally comprises from 1–15% by weight of the insecticidal composition.

Other useful formulations include simple solutions of the active ingredient in a solvent in which it is completely soluble at the desired concentration, such as acetone or other organic solvents.

The concentration of the toxicant in the dilution generally used for application is normally in the range of about 2% to about 0.001%. Many variations of spraying and dusting compositions in the art may be used, by substituting a compound of this invention into compositions known or apparent to the art.

Insecticidal compositions may be formulated and applied with other active ingredients, including other insecticides, nematicides, acaricides, fungicides, plant regulators, fertilizers, etc. In applying the chemicals, it is obvious that an effective amount and concentration of (methyl) (arylsulfenyl)carbamic acid ester of 2,3-dihydro-2,2-dimethyl-7-benzofuranol should be employed.

It is apparent that many modifications may be made in the structure, preparation, formulation and application of the compounds of this invention, without departing from the spirit and scope of the invention and of the following claims.

We claim:
1. The compound 2,3-dihydro-2,2-dimethyl-7-benzofuranyl (2-benzothiazolylthio) (methyl)carbamate.
2. The compound 2,3-dihydro-2,2-dimethyl-7-benzofuranyl (methyl)-(3,4-methylenedioxyphenylthio)carbamate.
3. The compound 2,3-dihydro-2,2-dimethyl-7-benzofuranyl (4-cyanophenylthio) (methyl)carbamate.

* * * * *

UNITED STATES PATENT OFFICE
CERTIFICATE OF CORRECTION

PATENT NO. : 3,997,549
DATED : December 14, 1976
INVENTOR(S) : Tetsuo Roy Fukuto and Allan L. Black It is certified that error appears in the above-identified patent and that said Letters Patent are hereby corrected as shown below:

Column 1, line 46, "centigrade," should read --centigrade.--.
Column 1, line 47, "concentation" should read --concentration--.
Column 2, line 53, "dro-2,-2-dimethy-7-benzofuranyl" should read --dro-2,2-dimethyl-7-benzofuranyl--.
Column 2, line 54, "phenylthio)-carbamate," should read --phenylthio)carbamate,--.
Column 3, line 43, "in 50 ml" should read --in 150 ml--.
Column 5, line 24, "(methyl)-(3,4-methylenedioxyphenylthio)carbamate" should read --(methyl)(3,4-methylenedioxyphenylthio)carbamate--.
Column 5, line 36, "(methyl)-(pentachlorophenylthio)carbamate" should read --(methyl)(pentachlorophenylthio)carbamate--.
Column 5, line 46, "(methyl)-(2-naphthylthio)carbamate" should read --(methyl)(2-naphthylthio)carbamate--.
Column 7, line 25, "foilage" should read --foliage--.
Column 8, line 56, "solution" should read --solution,--.
Column 9, line 40, "(arylsulfenyl)-carbamic" should read --(arylsulfenyl)carbamic--.

Column 10, line 44, "commence" should read --commerce--.
Column 12, line 1, "(methyl)-(3,4-methylenedioxyphenylthio)-" should read --(methyl)(3,4-methylenedioxyphenylthio)- --.

Signed and Sealed this

Seventh Day of June 1977

[SEAL]

*Attest:*

RUTH C. MASON
*Attesting Officer*

C. MARSHALL DANN
*Commissioner of Patents and Trademarks*